US012745894B1

(12) United States Patent
Shor et al.

(10) Patent No.: US 12,745,894 B1
(45) Date of Patent: Sep. 29, 2026

(54) TECHNIQUES FOR GENERATING SUPERRESOLUTION PRESENTATIONS OF MEDICAL PROCEDURE VIDEO DATA

(71) Applicant: Verily Life Sciences LLC, South San Francisco, CA (US)

(72) Inventors: Joel Shor, Tokyo (JP); Ehud Benyamin Rivlin, Haifa (IL); Daniel Freedman, Haifa (IL)

(73) Assignee: Verily Life Sciences LLC, Dallas, TX (US)

( * ) Notice: Subject to any disclaimer, the term of this patent is extended or adjusted under 35 U.S.C. 154(b) by 1297 days.

(21) Appl. No.: 17/566,493

(22) Filed: Dec. 30, 2021

Related U.S. Application Data

(60) Provisional application No. 63/200,684, filed on Mar. 22, 2021.

(51) Int. Cl.
*A61B 1/00* (2006.01)
*A61B 1/31* (2006.01)
(Continued)

(52) U.S. Cl.
CPC .. *A61B 1/000096* (2022.02); *A61B 1/000095* (2022.02); *A61B 1/00045* (2013.01);
(Continued)

(58) Field of Classification Search
CPC .... A61B 1/000095–1/000096; A61B 1/00045; A61B 1/31; G06T 7/70;
(Continued)

(56) References Cited

U.S. PATENT DOCUMENTS 10,510,144 B2 * 12/2019 Zur .................. A61B 1/000096
12,080,021 B2 * 9/2024 Le .......................... G16H 30/40
(Continued)

FOREIGN PATENT DOCUMENTS

CA 3092994 A1 * 9/2019 ............. G06N 3/048

OTHER PUBLICATIONS

Rahim, T., et al., A deep convolutional neural network for the detection of polyps in colonoscopy images, Biomedical Signal Processing and Control, vol. 68, 2021, 102654, ISSN 1746-8094. (Year: 2021).*

(Continued)

*Primary Examiner* — Nizar N Sivji
(74) *Attorney, Agent, or Firm* — Christensen O'Connor Johnson Kindness PLLC

(57) ABSTRACT

In some embodiments, a method of automatically generating high-resolution images of features of interest to accompany video data of a medical procedure of a given type is provided. A computing system provides the video data of the medical procedure to a first machine learning model trained to annotate features of interest. The computing system provides annotated portions of the video data to a second machine learning model trained on past images of features of interest to produce superresolution images of features of interest. The computing system generates a presentation of the video data of the medical procedure that includes the superresolution images of the features of interest produced by the second machine learning model.

17 Claims, 8 Drawing Sheets

(51) Int. Cl.
*G06T 7/70* (2017.01)
*G16H 30/40* (2018.01)

(52) U.S. Cl.
CPC .................. *A61B 1/31* (2013.01); *G06T 7/70* (2017.01); *G16H 30/40* (2018.01); *G06T 2207/20081* (2013.01); *G06T 2207/30032* (2013.01)

(58) Field of Classification Search
CPC G06T 2207/20081; G06T 2207/30032; G16H 30/40
See application file for complete search history.

(56) References Cited

U.S. PATENT DOCUMENTS

| | | | | |
|---|---|---|---|---|
| 2019/0057488 | A1* | 2/2019 | Li | G06T 7/136 |
| 2021/0098300 | A1* | 4/2021 | Kusunoki | H10D 88/00 |
| 2022/0335573 | A1* | 10/2022 | Zhu | G06T 3/4053 |
| 2023/0237619 | A1* | 7/2023 | Omi | G06T 3/4053 |
| 2026/0073718 | A1* | 3/2026 | Fouts | G06V 10/82 |

OTHER PUBLICATIONS

Y. Romano, J. Isidoro and P. Milanfar, “RAISR: Rapid and Accurate Image Super Resolution,” in IEEE Transactions on Computational Imaging, vol. 3, No. 1, pp. 110-125, Mar. 2017, doi: 10.1109/TCI.2016.2629284. (Year: 2017).*

Wang, X., et al., “ESRGAN: Enhanced Super-Resolution Generative Adversarial Networks”, arXiv:1809.00219v2 cs.CV], Sep. 17, 2018, pp. 1-17. (Year: 2018).*

Wronski, B., et al., “Handheld Multi-Frame Super-Resolution”, ACM Trans. Graph., vol. 38, No. 4, Article 28, Jul. 2019, pp. 28:1-28:18. (Year: 2019).*

Yang, W., et al., “Deep Leaming for Single Image Super-Resolution: A Brief Review”, arXiv:1808.03344v3 [cs.CV], Jul. 12, 2019, pp. 1-16. (Year: 2019).*

Freedman, D., et al., “Detecting Deficient Coverage in Colonoscopies”, enarXiv: 2001.08589v3 [cs.CV], Mar. 29, 2020, pp. 1-12. (Year: 2020).*

Almalioglu, Y., et al., “Endol2H: Deep Super-Resolution for Capsule Endoscopy”, arXiv:2002.05459v2 cs.CV], Jun. 22, 2020, pp. 1-23. (Year: 2020).*

Timofte, R., et al., “A+: Adjusted Anchored Neighborhood Regression for Fast Super-Resolution”, Asian conference on computer vision, Nov. 1, 2014, pp. 111-126. (Year: 2014).*

Lin, L., et al., “ESGAN: Edge Loss and Spatial Convolution Generative Adversarial Network for Image Inpainting,” 2020 IEEE 15th International Conference on Solid-State & Integrated Circuit Technology (ICSICT), Kunming, China, 2020, pp. 1-4, doi: 10.1109/ICSICT49897.2020.9278191. (Year: 2020).*

Rahim, T., Hassan, S. A., Shin, S. Y., & Kumoh National Institute of Technology. (2020). A deep convolutional neural network for the detection of polyps in colonoscopy images. Journal of LATEX Templates (Year: 2020).*

Romano, Y., et al., “RAISR: Rapid and Accurate Image Super Resolution”, arXiv:1606.01299v3 [cs.CV], Oct. 4, 2016, pp. 1-31.

Wang, X., et al., “ESRGAN: Enhanced Super-Resolution Generative Adversarial Networks”, arXiv:1809.00219v2 [cs.CV], Sep. 17, 2018, pp. 1-17.

Wronski, B., et al., “Handheld Multi-Frame Super-Resolution”, ACM Trans. Graph., vol. 38, No. 4, Article 28, Jul. 2019, pp. 28:1-28:18.

Yang, W., et al., “Deep Learning for Single Image Super-Resolution: A Brief Review”, arXiv:1808.03344v3 [cs.CV], Jul. 12, 2019, pp. 1-16.

Freedman, D., et al., “Detecting Deficient Coverage in Colonoscopies”, enarXiv: 2001.08589v3 [cs.CV], Mar. 29, 2020, pp. 1-12.

Almalioglu, Y., et al., “EndoL2H: Deep Super-Resolution for Capsule Endoscopy”, arXiv:2002.05459v2 [cs.CV], Jun. 22, 2020, pp. 1-23.

Timofte, R., et al., “A+: Adjusted Anchored Neighborhood Regression for Fast Super-Resolution”, Asian conference on computer vision, Nov. 1, 2014, pp. 111-126.

* cited by examiner

TECHNIQUES FOR GENERATING SUPERRESOLUTION PRESENTATIONS OF MEDICAL PROCEDURE VIDEO DATA

CROSS REFERENCE TO RELATED APPLICATION

This application claims the benefit of Provisional Application No. 63/200,684, filed Mar. 22, 2021, the entire disclosure of which is hereby incorporated by reference herein for all purposes.

TECHNICAL FIELD

This disclosure relates generally to surgical technologies, and in particular but not exclusively, relates to improvements in imagery obtained by surgical technologies.

BACKGROUND INFORMATION

Endoscopy allows a physician to view organs and cavities internal to a patient using an insertable instrument. This is a valuable tool for making diagnoses without needing to guess or perform exploratory surgery. The insertable instruments, sometimes referred to as endoscopes or borescopes, have a portion, such as a tube, that is inserted into the patient and positioned to be close to an organ or cavity of interest.

Endoscopes first came into existence in the early 1800s, and were used primarily for illuminating dark portions of the body (since optical imaging was in its infancy). In the late 1950s, the first fiber optic endoscope capable of capturing an image was developed. A bundle of glass fibers was used to coherently transmit image light from the distal end of the endoscope to a camera. Today, obtaining imagery from the distal end of the endoscope is a common use case for such technology.

BRIEF SUMMARY

In some embodiments, a method of automatically generating high-resolution images of features of interest to accompany video data of a medical procedure of a given type is provided. The method includes providing, by a computing system, the video data of the medical procedure to a first machine learning model trained to annotate features of interest, providing, by the computing system, annotated portions of the video data to a second machine learning model trained on past images of features of interest to produce superresolution images of features of interest, and generating, by the computing system, a presentation of the video data of the medical procedure that includes the superresolution images of the features of interest produced by the second machine learning model. The medical procedure of the given type may be a colonoscopy, and the features of interest may be polyps.

The presentation of the video data of the medical procedure that includes the superresolution images of the features of interest may include a zoomed inset version of at least one superresolution image.

Generating the presentation of the video data of the medical procedure that includes the superresolution images of the features of interest produced by the second machine learning model may include providing the video data of the medical procedure to a third machine learning model trained on video data of past medical procedures of the given type to produce superresolution video data, and generating a presentation that includes the superresolution video data.

The video data may be generated during the medical procedure, or may be generated after completion of the medical procedure. The first image and the second image may represent an entirety of the at least one frame.

The computer-implemented method may further include determining an annotated portion of the at least one frame that depicts a feature of interest; where the first image and the second image represent the annotated portion of the at least one frame and exclude portions of the at least one frame outside of the annotated portion. Determining the annotated portion of the at least one frame that depicts the feature of interest may include determining a first annotated portion of a first frame that depicts the feature of interest from a first distance, determining a second annotated portion of a second frame that depicts the feature of interest from a second distance, and scaling at least one of the first annotated portion of the first frame and the second annotated portion of the second frame to be of matching sizes.

Generating at least the first image in the first resolution and the second image in the second resolution may include generating the first image at a native resolution of the video data record, and generating the second image by downsampling the first image. The video data record may include frames in the first resolution and frames in the second resolution; and generating at least the first image in the first resolution and the second image in the second resolution may include determining a transition in the video data record from the first resolution to the second resolution, generating the first image at the first resolution based on a frame before the transition, and generating the second image at the second resolution based on the frame after the transition.

The second machine learning model may be a RAISR model, a SABRE model or an ESRGAN model.

In some embodiments, a computer-readable medium having logic stored thereon is provided. The logic, in response to execution by one or more processors of a computing system, cause the computing system to perform actions of a method as described above. In some embodiments, a computing system including such a computer-readable medium with such logic stored thereon is provided.

BRIEF DESCRIPTION OF THE SEVERAL VIEWS OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described. To easily identify the discussion of any particular element or act, the most significant digit or digits in a reference number refer to the figure number in which that element is first introduced.

DETAILED DESCRIPTION

Figure 1:
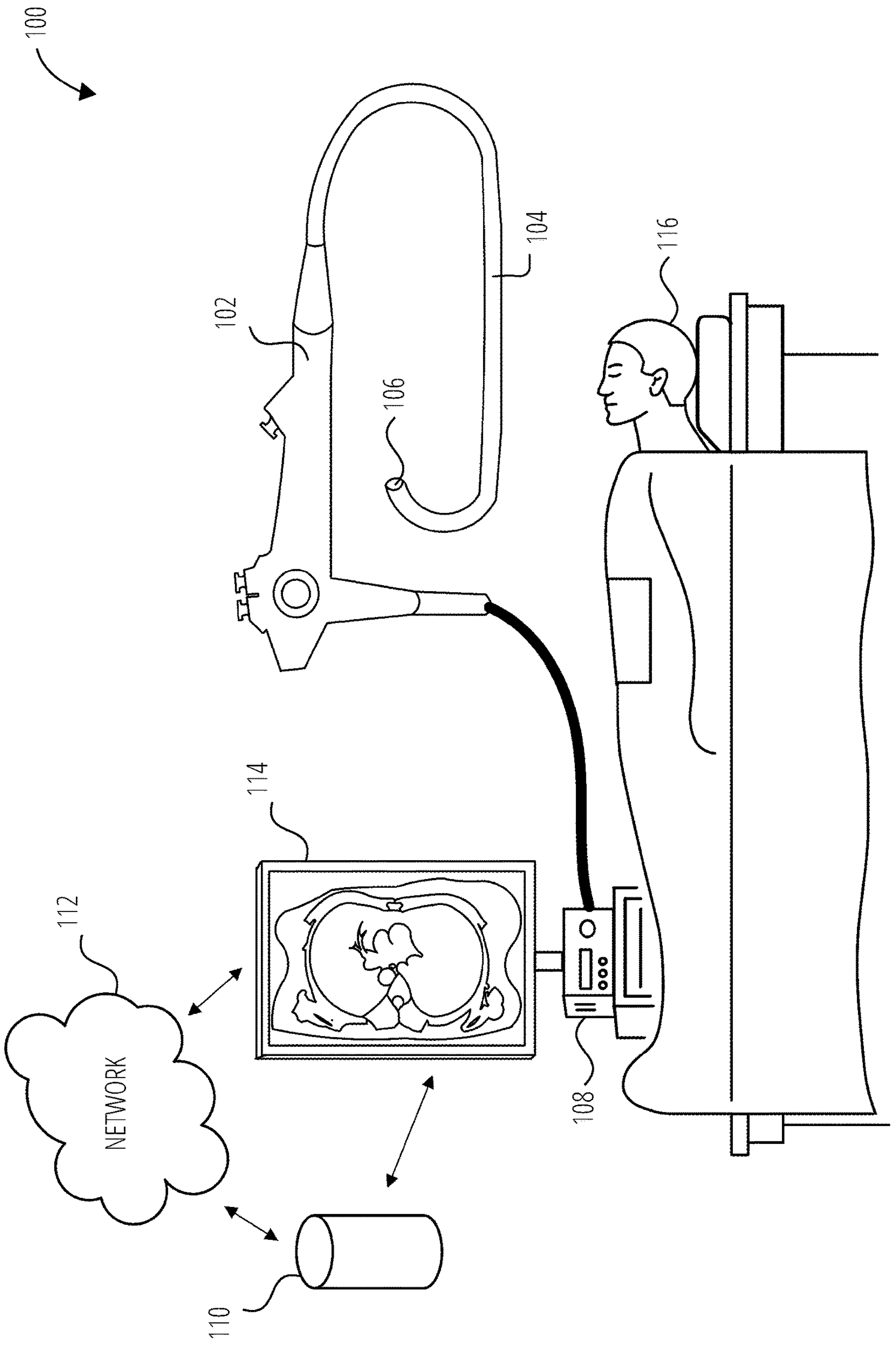
FIG. 1 illustrates a non-limiting example embodiment of an endoscope system according to various aspects of the present disclosure.

FIG. 1 illustrates a non-limiting example embodiment of an endoscope system 100, according to various aspects of the present disclosure. Endoscope system 100 includes endoscope 102 (with endoscope tube 104 extending from the endoscope 102 to a distal tip 106), computing system 108, data store 110, network 112, and display device 114. It is appreciated that a controller within or associated with the endoscope 102 may include elements of computing system 108, data store 110, network 112, and/or display device 114, as well as control circuitry and software for operating the endoscope 102. Put another way, the endoscope system 100 may be a distributed system where different actions occur in different locations and/or are performed by different devices (e.g., in endoscope 102, in computing system 108, and/or on remote servers), in accordance with the teachings of the present disclosure. As shown, all components depicted are coupled by wires or wirelessly.

As shown, the endoscope system 100 obtains imagery from the distal tip 106 via a camera (not illustrated) while the endoscope tube 104 is inserted within a subject 116, and generates presentations of the imagery using the display device 114. In some embodiments, network 112, data store 110, and computing system 108 may provide image processing functionality using techniques including, but not limited to, machine learning techniques. In some embodiments, the computing system 108 may perform some amount of image processing, communicate with the data store 110 and/or the network 112, and control various operational aspects of the endoscope 102 (including but not limited to the amount of light output from distal tip 106, a resolution of imagery obtained, and/or a contrast level of the imagery received from the camera).

As shown, the proximal (hand-held) portion of the endoscope 102 may have a number of buttons, joysticks, or other human-machine interaction devices to control movement of distal tip 106, articulation of the endoscope tube 104, and/or other aspects of the operation of the endoscope system 100. One of ordinary skill in the art will appreciate that endoscope 102 depicted here is merely a cartoon illustration of an endoscope, and that the term “endoscopy” should encompass all types of endoscopy (e.g., colonoscopy, laparoscopy, endoscopy, robotic surgery, or any other situation when a camera is inserted into a body), and that an endoscope should include at least “chip-on-a-tip” devices, rod lens devices (ridged), image fiber devices (flexible) to name a few. In some embodiments, endoscope 102 may be included in surgical robotic systems or coupled to a surgical robot.

While endoscopy has been found to be hugely beneficial in allowing the practice of minimally invasive procedures, challenges remain in maximizing the effectiveness of such procedures. One limitation of existing systems is that the imagery generated by existing systems may be of too low of a resolution for clinically significant use.

For example, one common endoscopic procedure is colonoscopy. Colorectal cancer (CRC) is the second most common cause of cancer in women (9.2% of diagnoses) and the third most common in men (10.0%) globally. Most cases are linked to a “Western” lifestyle with genetics thought to play a more limited role. While cases of CRC in the US peaked in the 1980s, they have been increasing in other locations, including Japan. Colonoscopy, both through screening programs and through opportunistic procedures, is an important tool in identifying these cancers early enough to treat patients.

During a colonoscopy, a physician views a presentation of images of the colon obtained from the distal tip of the endoscope. The physician examines the images to look for areas that may be considered a polyp, which may then be biopsied, excised, or otherwise treated. The physician may use shape or texture in order to diagnose polyps on the wall of the colon.

There are several techniques that can help improve the likelihood that the physician will correctly diagnose polyps during a colonoscopy. For example, accuracy of diagnoses is improved by providing higher resolution imagery to the physician. By viewing a high-resolution image, a physician can not only detect potential polyps, but can use shape, color, depression, and other factors to perform an “optical biopsy” of potential polyps to determine polyp types (e.g., non-neoplastic types such as hyperplastic polyps, inflammatory polyps, and hamartomatous polyps, or neoplastic types such as adenomas and serrated types). As another example, computer vision techniques can be used to detect potential polyps in video generated by the endoscope, and the potential polyps can be annotated to draw the physician’s attention.

In order to provide such functionality, embodiments of the present disclosure use superresolution techniques to improve the quality of the imaging produced by endoscope systems. Superresolution imaging, or SR, processes a source image to generate an enhanced image with a higher resolution. SR can be used to generate enhanced images with resolutions higher than can be generated by a digital image sensor used to capture source images. These higher resolution images can allow physicians to provide more accurate diagnoses, and can be provided to computer vision models to provide more accurate annotations of potential polyps.

Figure 2:
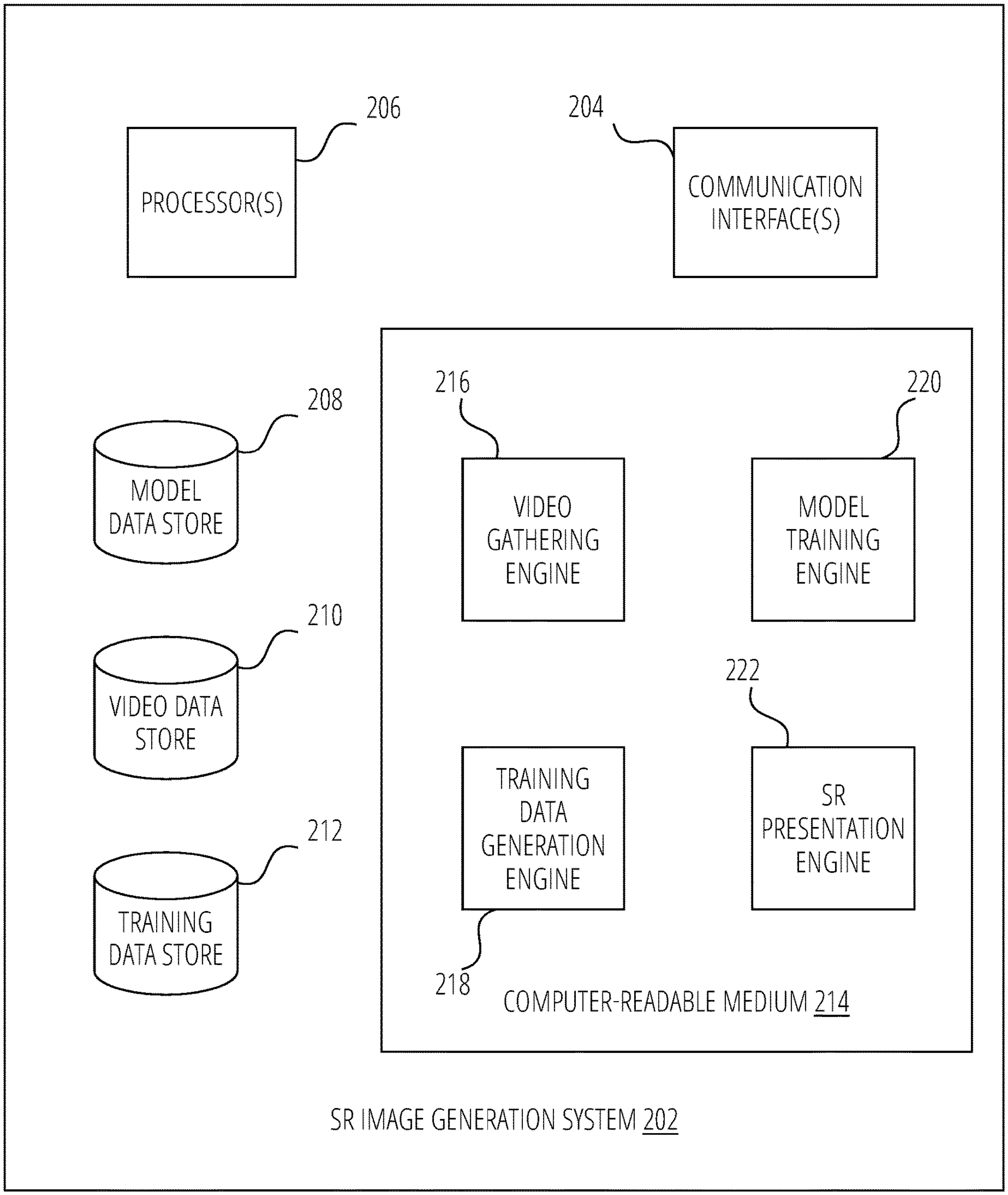
FIG. 2 is a block diagram that illustrates a non-limiting example embodiment of a superresolution (SR) image generation system according to various aspects of the present disclosure.

FIG. 2 is a block diagram that illustrates a non-limiting example embodiment of a superresolution (SR) image generation system according to various aspects of the present disclosure. Unlike some other systems, the SR image generation system 202 trains machine learning models to produce SR images using video data collected during similar past procedures. Using video for training (instead of standard images that are used in some benchmark systems that use computer vision to detect features of interest) helps improve accuracy by exposing the machine learning algorithms to many more examples of both normal tissue and features of interest. Further, by using video data that depicts other examples of the types of tissues and features of interest for training instead of more generic types of video data, more accurate SR images can be generated.

In some embodiments, the SR image generation system 202 may be provided by a single computing device, including but not limited to a desktop computing device, a laptop computing device, a mobile computing device, an embedded computing device, a server computing device, or a computing device of a cloud computing system. In some embodiments, the SR image generation system 202 may be provided by multiple computing devices of the same or different types working together to provide the described components. In the illustrated embodiment, the SR image generation system 202 includes one or more processors 206, one or more communication interfaces 204, a model data store 208, a video data store 210, a training data store 212, and a computer-readable medium 214.

In some embodiments, the processors 206 may include any suitable type of general-purpose computer processor. In some embodiments, the processors 206 may include one or more special-purpose computer processors or AI accelerators optimized for specific computing tasks, including but not limited to graphical processing units (GPUs), vision processing units (VPUs), and tensor processing units (TPUs).

In some embodiments, the communication interfaces 204 include one or more hardware and/or software suitable for providing communication links between the SR image generation system 202 and other devices, including but not limited to components of the endoscope system 100, the display device 114, and the network 112. The communication interfaces 204 may support one or more wired communication technologies (including but not limited to Ethernet, FireWire, USB, HDMI, DVI, and VGA), one or more wireless communication technologies (including but not limited to Wi-Fi, Bluetooth, 5G, 4G, and LTE), or combinations thereof.

As used herein, "computer-readable medium" refers to a removable or nonremovable device that implements any technology capable of storing information in a volatile or non-volatile manner to be read by a processor of a computing device, including but not limited to: a hard drive; a flash memory; a solid state drive; random-access memory (RAM); read-only memory (ROM); a CD-ROM, a DVD, or other disk storage; a magnetic cassette; a magnetic tape; and a magnetic disk storage.

As shown, the computer-readable medium 214 has logic stored thereon that, in response to execution by the one or more processors 206, cause the SR image generation system 202 to provide a video gathering engine 216, a training data generation engine 218, a model training engine 220, and an SR presentation engine 222.

As used herein, "engine" refers to logic embodied in hardware or software instructions, which can be written in one or more programming languages, including but not limited to C, C++, C#, COBOL, JAVA™, PHP, Perl, HTML, CSS, JavaScript, VBScript, ASPX, Go, and Python. An engine may be compiled into executable programs or written in interpreted programming languages. Software engines may be callable from other engines or from themselves. Generally, the engines described herein refer to logical modules that can be merged with other engines, or can be divided into sub-engines. The engines can be implemented by logic stored in any type of computer-readable medium or computer storage device and be stored on and executed by one or more general purpose computers, thus creating a special purpose computer configured to provide the engine or the functionality thereof. The engines can be implemented by logic programmed into an application-specific integrated circuit (ASIC), a field-programmable gate array (FPGA), or another hardware device.

In some embodiments, the video gathering engine 216 is configured to obtain video data and to store it in the video data store 210. In some embodiments, the video gathering engine 216 may retrieve video data of previously conducted medical procedures for storage in the video data store 210. In some embodiments, the video gathering engine 216 may receive video data generated by an endoscope system 100 during a medical procedure.

In some embodiments, the training data generation engine 218 is configured to use the video data stored in the video data store 210 to generate training data for training one or more machine learning models, and to store the generated training data in the training data store 212. For machine learning models that generate superresolution images, the training data typically includes images in multiple different resolutions based on frames of the video data. As mentioned above, because the training data generation engine 218 operates on video data, a large amount of training data can be generated based on a relatively smaller number of instances of video data. In one non-limiting example embodiment, 5,000 instances of video data of a total of 1,000 hours can result in 110,000,000 frames to be converted into instances of training data.

In some embodiments, the model training engine 220 is configured to use the training data stored in the training data store 212 to train one or more machine learning models to generate SR images based on video data (or individual frames of video data, or images generated based on individual frames of video data), and to store the resulting machine learning models in a model data store 208. In some embodiments, the model training engine 220 may be configured to train different machine learning models for different medical procedures or features of interest. In some embodiments, the model training engine 220 may be configured to train machine learning models of multiple different architectures, depending on the intended use. For example, a first machine learning model with a first architecture that offers high speed but comparatively lower SR performance may be used to generate a real-time SR presentation during a procedure, and a second machine learning model with a second architecture that offers lower speed but comparatively higher SR performance may be used to generate an offline SR presentation after a procedure is completed.

In some embodiments, the SR presentation engine 222 is configured to use the machine learning models stored in the model data store 208 to process video data of a medical procedure and create a presentation that includes SR images. Further description of the configuration of each of these components is provided below.

As used herein, "data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure.

Figure 3A:
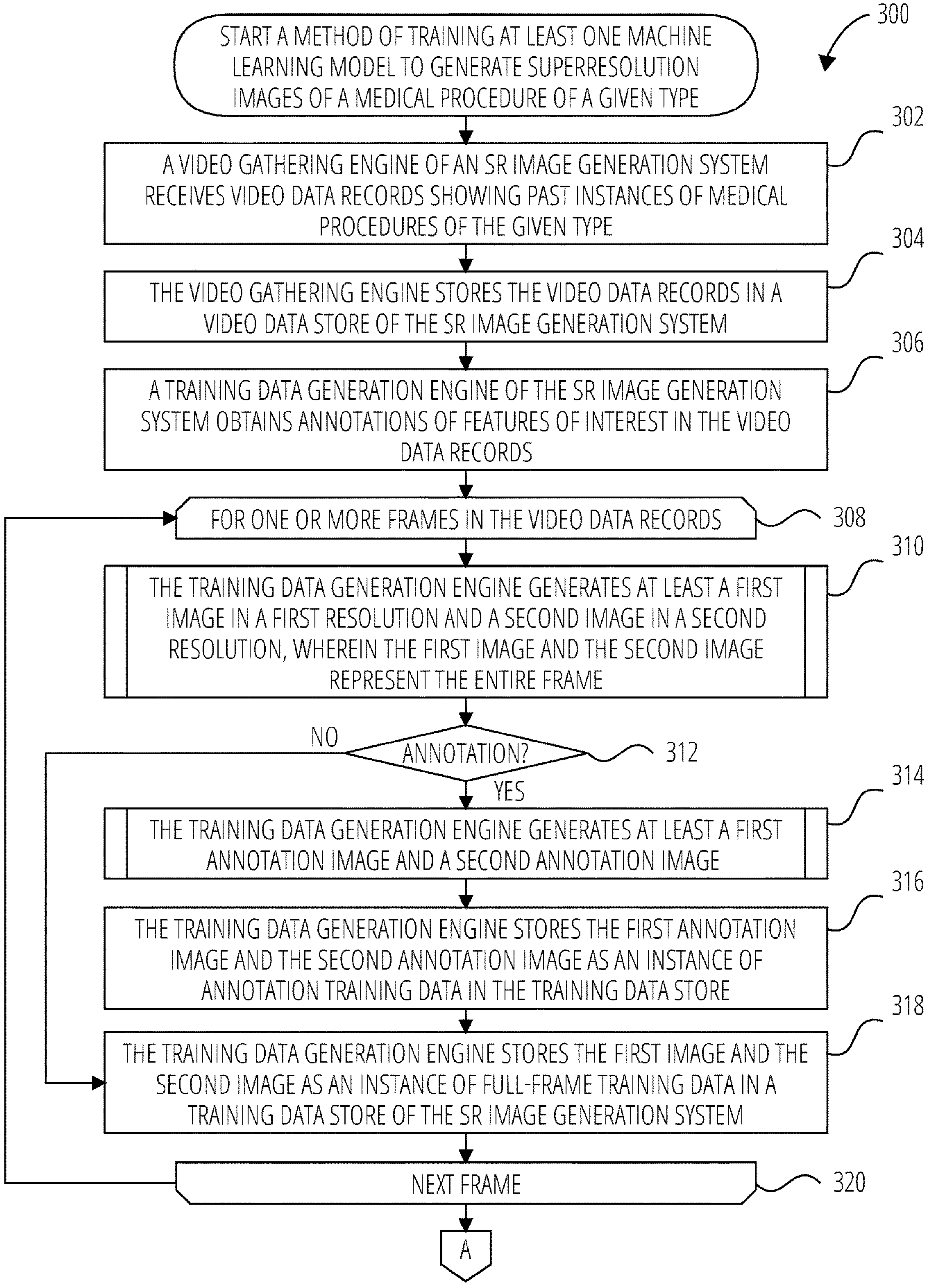
FIG. 3A-FIG. 3B are a flowchart that illustrates a non-limiting example embodiment of a method of training at least one machine learning model to generate superresolution (SR) images of a medical procedure of a given type, according to various aspects of the present disclosure.
Figure 3B:
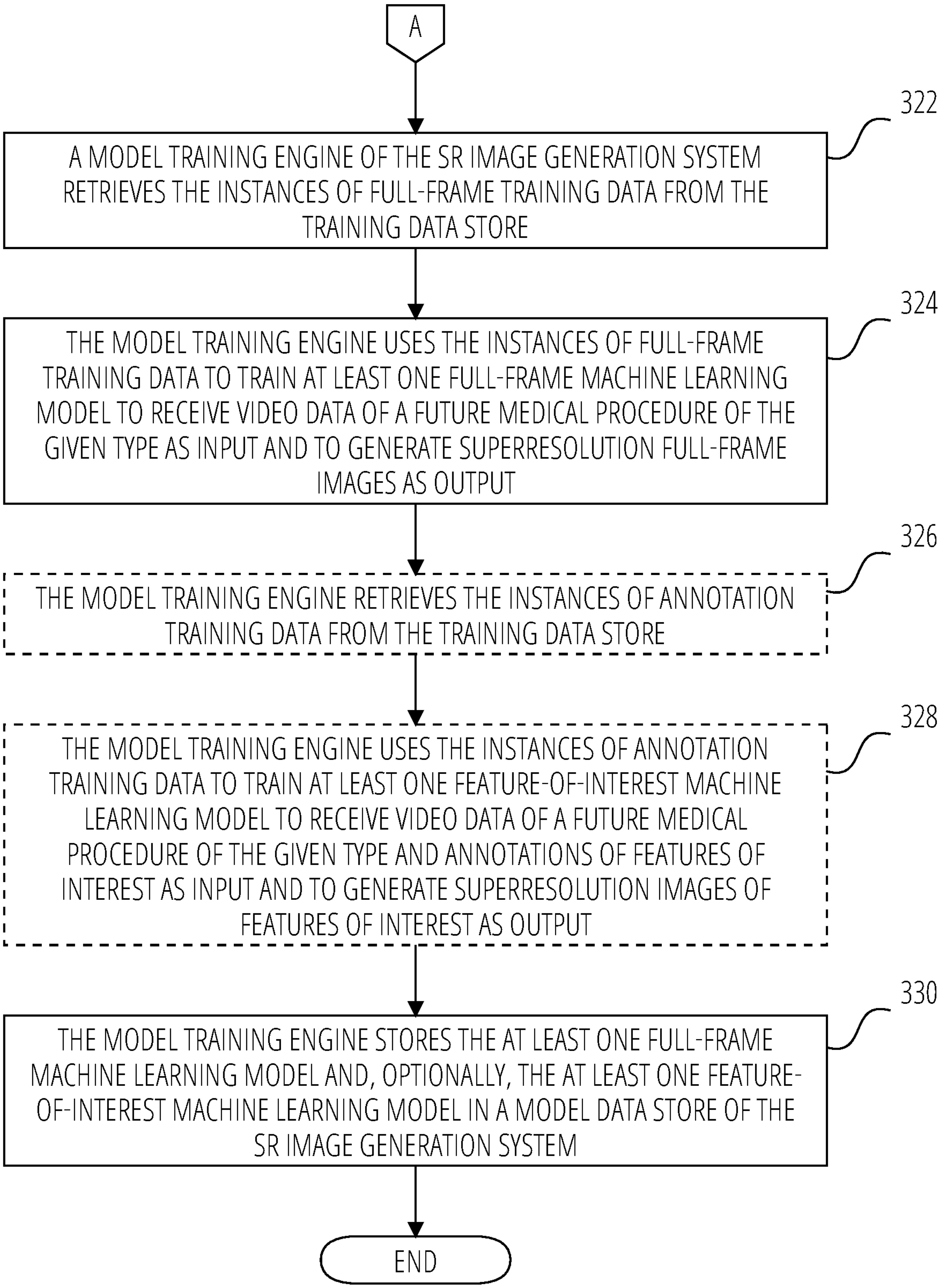

FIG. 3A-FIG. 3B are a flowchart that illustrates a non-limiting example embodiment of a method of training at least one machine learning model to generate superresolution (SR) images of a medical procedure of a given type, according to various aspects of the present disclosure. By training machine learning models on training data derived from previous medical procedures of the given type, highly performant machine learning models may be obtained for future medical procedures of the given type. As a non-limiting example, to train machine learning models to generate SR images during colonoscopies, the method 300 may use video data generated during previous colonoscopies.

From a start block, the method 300 proceeds to block 302, where a video gathering engine 216 of an SR image generation system 202 receives video data records showing past instances of medical procedures of the given type, and at block 304, the video gathering engine 216 stores the video data records in a video data store 210 of the SR image generation system 202. In some embodiments, the video gathering engine 216 may use one or more communication interfaces 204 to retrieve the video data records from other endoscope systems 100 that had recorded the video data during previous procedures of the same given type.

At block 306, a training data generation engine 218 of the SR image generation system 202 obtains annotations of features of interest in the video data records. The annotations may indicate portions of the video data that depict features of interest. As a non-limiting example, for video data that depicts a colonoscopy, the annotation information may indicate portions of frames of the video data that depict a polyp or a potential polyp. In some embodiments, the training data generation engine 218 may obtain annotations of features of interest in the video data records by providing the video data to machine learning models that have already been trained to detect the features of interest in video data. In some embodiments, the training data generation engine 218 may obtain annotations of features of interest in the video data records that are manually added by experts, including but not limited to annotations added by physicians upon reviewing the video data. In some embodiments, the video data records received by the video gathering engine 216 may already include annotation information, in which case the training data generation engine 218 does not need to perform further actions to obtain the annotations.

The method 300 then proceeds to a for-loop defined between a for-loop start block 308 and a for-loop end block 320, wherein frames of each instance of video data are processed to generate training data. In some embodiments, all of the frames of every instance of video data are processed in the for-loop. In some embodiments, a sampling of fewer than all of the frames of every instance of video data are processed.

As discussed above, machine learning models generate higher quality SR images if they are trained on data similar to the data that will be processed. Further, the textures present in a majority of the imagery in the video data may be different from textures present in features of interest. Accordingly, one goal of the for-loop is to generate separate sets of training data for generating SR images for an entire frame of video data and for generating SR images for annotated portions of video data that depict features of interest so that both types of imagery may have the best possible SR images generated.

From for-loop start block 308, the method 300 proceeds to subroutine block 310, where the training data generation engine 218 generates at least a first image in a first resolution and a second image in a second resolution, wherein the first image and the second image represent the entire frame. Typically, at least one of the first resolution and the second resolution is a native resolution in which the frame was captured, and the other resolution is a lower resolution. In any case, the first resolution and the second resolution are different, and the machine learning models are trained to predict the higher-resolution image based on the lower-resolution image. Any suitable procedure may be used to generate the first image and the second image, including but not limited to the procedures 412 and 414 described below. In some embodiments, more than two images at different resolutions may be generated for the frame by the procedure at subroutine block 310.

The method 300 then proceeds to decision block 312, where a determination is made regarding whether there is an annotation associated with the frame. In some embodiments, any annotation associated with the frame may be determined to be adequate. In some embodiments, the annotations may be associated with a confidence value that indicates how confident the physician (and/or a previous machine learning model) was that the region depicts a feature of interest, and only annotations that are associated with a confidence value that is greater than a threshold confidence value may be considered.

If an annotation is determined to be associated with the frame, then the result of decision block 312 is YES, and the method 300 advances to subroutine block 314. At subroutine block 314, the training data generation engine 218 generates at least a first annotation image and a second annotation image. Typically, the annotation indicates an annotated portion of the frame that depicts a feature of interest. The first annotation image and the second annotation image exclude the portions of the frame that are outside of the annotated portion, and are again of different resolutions.

Any suitable procedure may be used in subroutine block 314 for generating the first annotation image and the second annotation image. In some embodiments, a simple procedure may be used wherein the training data generation engine 218 determines a portion of the first image that is aligned with the annotated portion of the frame, extracts that portion of the first image as the first annotation image, and similarly extracts a portion of the second image that is aligned with the annotated portion of the frame to be used as the second annotation image. In some embodiments, more complicated procedures, including but not limited to the procedure illustrated in FIG. 5 and described below may be used.

Though the discussion of subroutine block 314 mentions only a single annotation in the frame, in some embodiments, if a frame contains multiple annotations, the procedure at subroutine block 314 may be executed to create images for each annotation. Likewise, in some embodiments, more than two annotation images at different resolutions may be generated for each annotation in the frame.

At block 316, the training data generation engine 218 stores the first annotation image and the second annotation image as an instance of annotation training data in the training data store. Again, if more than a first annotation image and a second annotation image were generated at subroutine block 314, then all of the annotation images will be stored in the instance of annotation training data.

The method 300 then proceeds from block 316 to block 318. Returning to decision block 312, if no annotation is determined to be associated with the frame, then the method 300 also proceeds directly to block 318 (skipping over subroutine block 314 and block 316).

In block 318, the training data generation engine 218 stores the first image and the second image as an instance of full-frame training data in a training data store 212 of the SR image generation system 202. Naturally, if more than a first image and a second image were created at subroutine block 310, then all of the images will be stored in the instance of full-frame training data.

The method 300 then proceeds to for-loop end block 320. If further frames remain to be processed, then the method 300 returns to for-loop start block 308 to process the next frame. Otherwise, the method 300 proceeds to a continuation terminal ("terminal A").

From terminal A (FIG. 3B), the method 300 proceeds to block 322, where a model training engine 220 of the SR image generation system 202 retrieves the instances of full-frame training data from the training data store 212. At block 324, the model training engine 220 uses the instances of full-frame training data to train at least one full-frame machine learning model to receive video data of a future medical procedure of the given type as input and to generate superresolution (SR) full-frame images as output.

Any suitable type of machine learning model may be trained to generate the SR full-frame images. One non-limiting example embodiment of a suitable machine learning model is a Rapid and Accurate Image Super Resolution (RAISR) model. RAISR uses a cheap upscaling algorithm (e.g. bilinear-interpolation) and applies filters trained by the model training engine 220 to enhance the upscaled image. RAISR focuses on lowering the computational complexity to provide fast upscaling. In some embodiments, the image is divided into patches and for each patch, RAISR learns a number of filters. The number of filters per patch depends on the scaling factor, and is typically the square of the scaling factor. A number of trained filters corresponds to a number of pixel types introduced by cheap upscaling. In some embodiments, the training is performed using a standard minimization of the Euclidean distance between the produced SR image and the goal image.

In some embodiments, a number of optimization techniques may be used by RAISR to speed up both training and execution. One non-limiting example of these techniques is to use an efficient hashing mechanism. The hashing mechanism uses local gradient statistics to generate keys for patches. The entries in the hash table would then be the set of trained filters applied to each pixel type. Another non-limiting example of a technique to refine the quality of the produced images is to incorporate sharpening and removing compression artifacts in the trained filters. The final step used in RAISR is to apply a blending algorithm. The blending process uses Census Transform and Difference of Gaussians to compute how likely a pixel is an artifact of the sharpening step. If that likelihood is greater than a threshold likelihood value, RAISR falls back and uses the cheap upscale. Otherwise, the trained filters and sharpening filters are applied. Further details regarding the training and use of RAISR models are known to those of those of ordinary skill in the art.

Another non-limiting example embodiment of a suitable machine learning model for generating SR full-frame images is a SABRE model. In a SABRE model, slight differences between adjacent frames that are introduced by a tremor in the video capture device are used to create the superresolution images. For such models, instead of using sets of images of different resolutions as the training data, the training data generation engine 218 may store sets of images from adjacent frames as instances of training data in order to provide the information needed by the algorithm.

Still another non-limiting example embodiment of a suitable machine learning model for generating SR full-frame images is an enhanced superresolution generative adversarial network (ESRGAN). GANs offer an implicit optimization strategy in an adversarial training way by using deep artificial neural networks. It uses the objective function to implicitly address optimization deep architectures in a game theory scenario, and successfully avoids the troubling approximate inference and approximation of the partition function gradient. The objective function is formed by the generator supervised by an auxiliary discriminator. The two parts update alternately. When the discriminator cannot give useful information to the generator anymore, the optimization procedure is completed.

Instead of focusing on minimizing the mean squared reconstruction error, the ESRGAN mainly solves the problem of recovering better texture details while getting the superresolution image. To achieve this, a perceptual loss function is used to train the model so that the superresolved image can have photo-realistic textures that are very similar to the original image. The perceptual loss function includes an adversarial loss and a content loss.

The content loss uses a loss function that is closer to perceptual similarity. The VGG loss is used to do the calculation. It is based on the ReLU activation layers of the pre-trained 19 layer VGG network. The adversarial loss is to encourage the network to favor solutions that reside on the manifold of nature images by trying to fool the discriminator network. The loss function is defined based on the probabilities (the reconstructed image is a natural HR image) of the discriminator over all instances of training data.

Each of the non-limiting examples of machine learning models described above have various strengths and weaknesses. For example, RAISR has a very fast execution time and is therefore highly appropriate for real-time generation of SR images based on incoming video data, but does not usually provide a large increase in resolution. In comparison, ESRGAN can be trained to provide a large increase in resolution, but operates slowly and is more suitable for offline processing. Accordingly, the model training engine 220 may train more than one type of machine learning model based on the training data to be used for different purposes.

At optional block 326, the model training engine 220 retrieves the instances of annotation training data from the training data store 212, and at optional block 328, the model training engine 220 uses the instances of annotation training data to train at least one feature-of-interest machine learning model to receive video data of a future medical procedure of the given type and annotations of features of interest as input and to generate superresolution images of features of interest as output. At this optional block 326, the model training engine 220 may use similar types of machine learning models and similar techniques for training as those discussed above with respect to the full-frame machine learning models in block 324, but with the instances of annotation training data as the training data instead of the instances of full-frame training data. In some embodiments, the model training engine 220 may train the same types of machine learning models as were trained in block 324, while in other embodiments, the model training engine 220 may train more, fewer, or different types of machine learning models than those trained in block 324.

At block 330, the model training engine 220 stores the at least one full-frame machine learning model and, optionally, the at least one feature-of-interest machine learning model in a model data store 208 of the SR image generation system 202. The method 300 then proceeds to an end block and terminates.

Figure 4A:
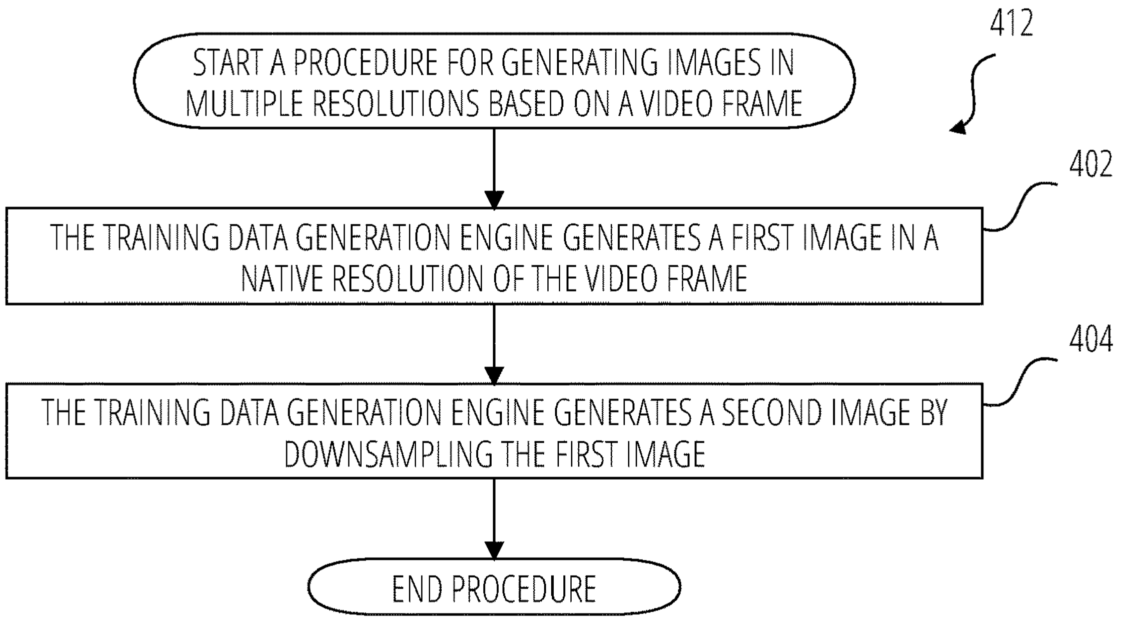
FIG. 4A-FIG. 4B are flowcharts that illustrate various non-limiting example embodiments of procedures for generating images in multiple resolutions based on a video frame according to various aspects of the present disclosure.
Figure 4B:
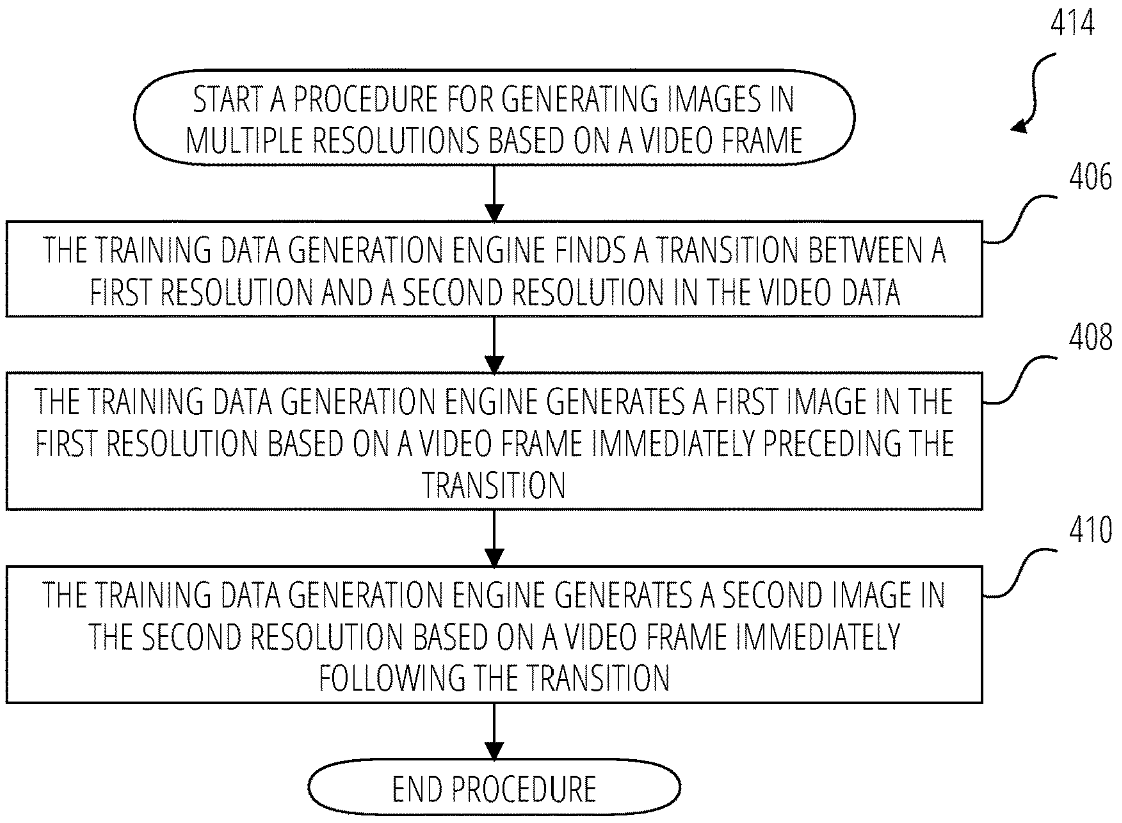

FIG. 4A-FIG. 4B are flowcharts that illustrate various non-limiting example embodiments of procedures for generating images in multiple resolutions based on a video frame according to various aspects of the present disclosure.

In FIG. 4A, a procedure 412 is illustrated in which images in multiple resolutions are generated from a single frame of the video data. From a start block, the procedure 412 advances to block 402, where the training data generation engine 218 generates a first image in a native resolution of the video frame.

At block 404, the training data generation engine 218 generates a second image by downsampling the first image. Any suitable downsampling technique may be used, which include but are not limited to using box filters, interpolation, Gaussian pyramid techniques, and Laplace pyramid techniques.

The procedure 412 then advances to an end block and returns control to its caller, providing the first image and the downsampled second image as a result. In some embodiments, the procedure 412 may generate more than one image by downsampling the first image by different amounts, and may provide the first image and all of the downsampled images as a result.

In FIG. 4B, a procedure 414 is illustrated that is useful if frames in multiple resolutions are present in the video data. In some endoscope systems 100, an operator is allowed to switch the endoscope 102 back and forth between a high-resolution mode and a low-resolution mode during the medical procedure. In video data generated by such endoscope systems 100, frames immediately preceding and immediately following the transition between the high-resolution mode and the low-resolution mode will depict at least some of the same features at the two different resolutions.

From a start block, the procedure 414 advances to block 406, where the training data generation engine 218 finds a transition between a first resolution and a second resolution in the video data. In some embodiments, the video data may be flagged to indicate such transitions. In some embodiments, the training data generation engine 218 may inspect the resolutions of frames of the video data in order to find the transitions.

At block 408, the training data generation engine 218 generates a first image in the first resolution based on a video frame immediately preceding the transition, and at block 410, the training data generation engine 218 generates a second image in the second resolution based on a video frame immediately following the transition. Because the resolutions preceding and following the transition are different, the resulting first image and second image will also be in different resolutions.

Typically, the higher-resolution image will have a smaller field of view than the lower-resolution image. In such embodiments, the training data generation engine 218 may crop the lower resolution image to contain only the portion that is visible in the higher-resolution image, and may perform registration techniques to align the two images with each other.

The procedure 414 then advances to an end block and returns control to its caller, providing the first image and the second image as a result.

Figure 5:
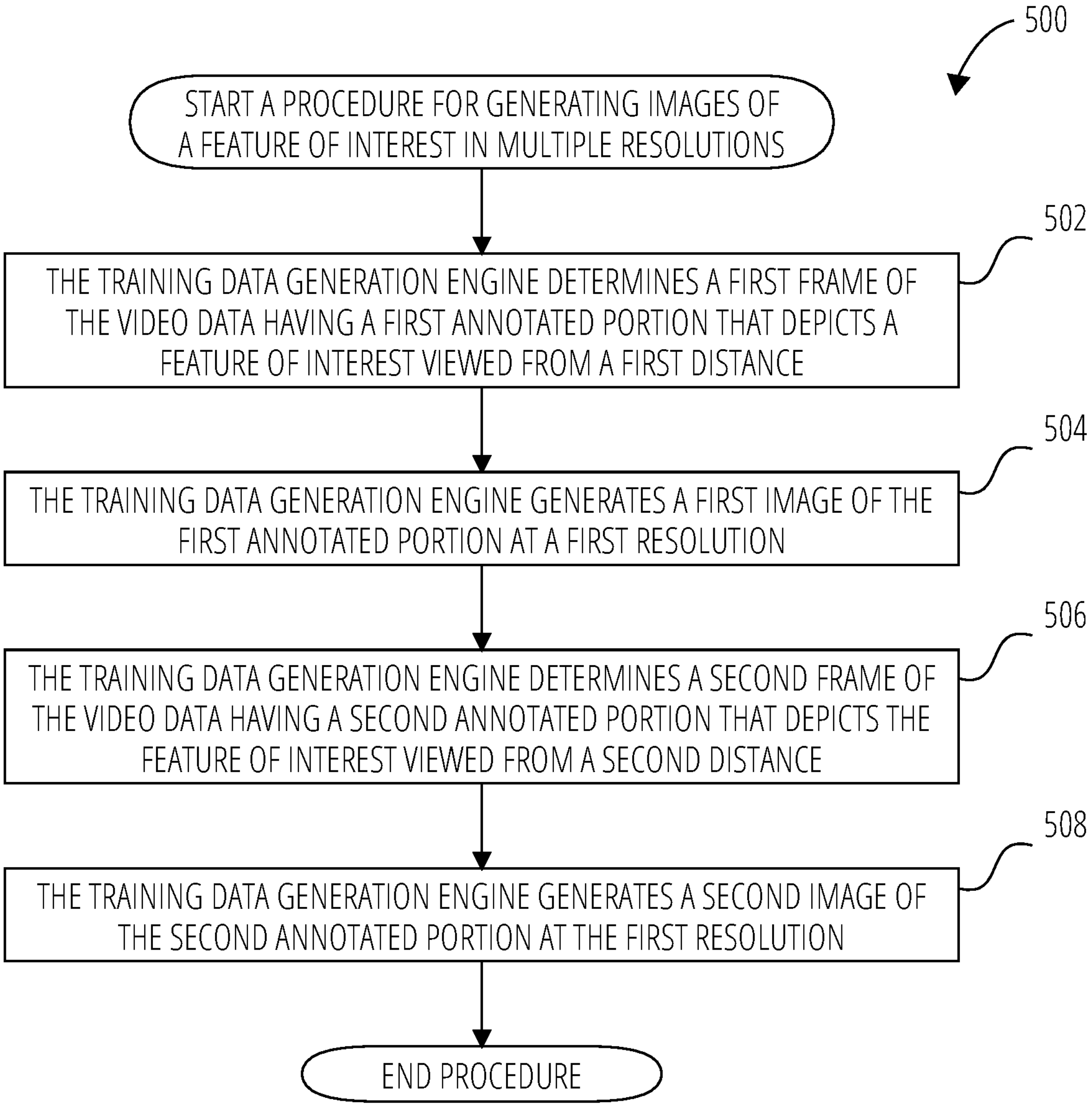
FIG. 5 is a flowchart that illustrates a non-limiting example embodiment of a procedure for generating images of a feature of interest in multiple resolutions according to various aspects of the present disclosure.

FIG. 5 is a flowchart that illustrates a non-limiting example embodiment of a procedure for generating images of a feature of interest in multiple resolutions according to various aspects of the present disclosure. The procedure 500 is a non-limiting example embodiment of a procedure suitable for use at subroutine block 314 of FIG. 3A.

From a start block, the procedure 500 advances to block 502, where the training data generation engine 218 determines a first frame of the video data having a first annotated portion that depicts a feature of interest viewed from a first distance. In some embodiments, the first frame may be provided as input to the procedure 500. As discussed above, the video data may be accompanied by annotation data that indicates the annotated portions of the frames. In some embodiments, the annotation data may include an identifier of the annotation, such that annotations of the same feature can be associated with each other in multiple frames.

At block 504, the training data generation engine 218 generates a first image of the first annotated portion at a first resolution. In some embodiments, the first image depicts the first annotated portion while excluding the remainder of the first frame, and is in the same resolution in which the frame was captured or is stored in the video data.

At block 506, the training data generation engine 218 determines a second frame of the video data having a second annotated portion that depicts the feature of interest viewed from a second distance. In embodiments wherein each feature is annotated with a matching identifier in all frames in which it is depicted, the second frame may be determined by finding another frame with an annotated portion associated with the same identifier as the first annotated portion. In some embodiments, the training data generation engine 218 may track movement of an annotated portion between frames in order to determine annotated portions in other frames that depict the same feature of interest as the first annotated portion of the first frame. In some embodiments, the training data generation engine 218 may choose the first frame as a frame in which the feature of interest is fully visible and is largest (e.g., closest to the distal tip 106 of the endoscope 102), and may choose the second frame as a frame in which the feature of interest is fully visible and is smallest (e.g., farthest from the distal tip 106 of the endoscope 102).

At block 508, the training data generation engine 218 generates a second image of the second annotated portion at the first resolution. Again, in some embodiments, the second image depicts the second annotated portion while excluding the remainder of the second frame, and is in the same resolution in which the frame was captured or is stored in the video data.

The procedure 500 then advances to an end block and returns control to its caller, with the first image and the second image being provided as a result of the procedure 500. As is evident, since the first image and the second image depict the same feature of interest in different sizes but the same resolution, the first image and the second image can be considered a high resolution and a low resolution version of the same feature of interest, and can therefore be used as an instance of training data in which the low resolution image (i.e., the smaller image) can be used to predict the details visible in the high resolution image (i.e., the larger image).

Figure 6:
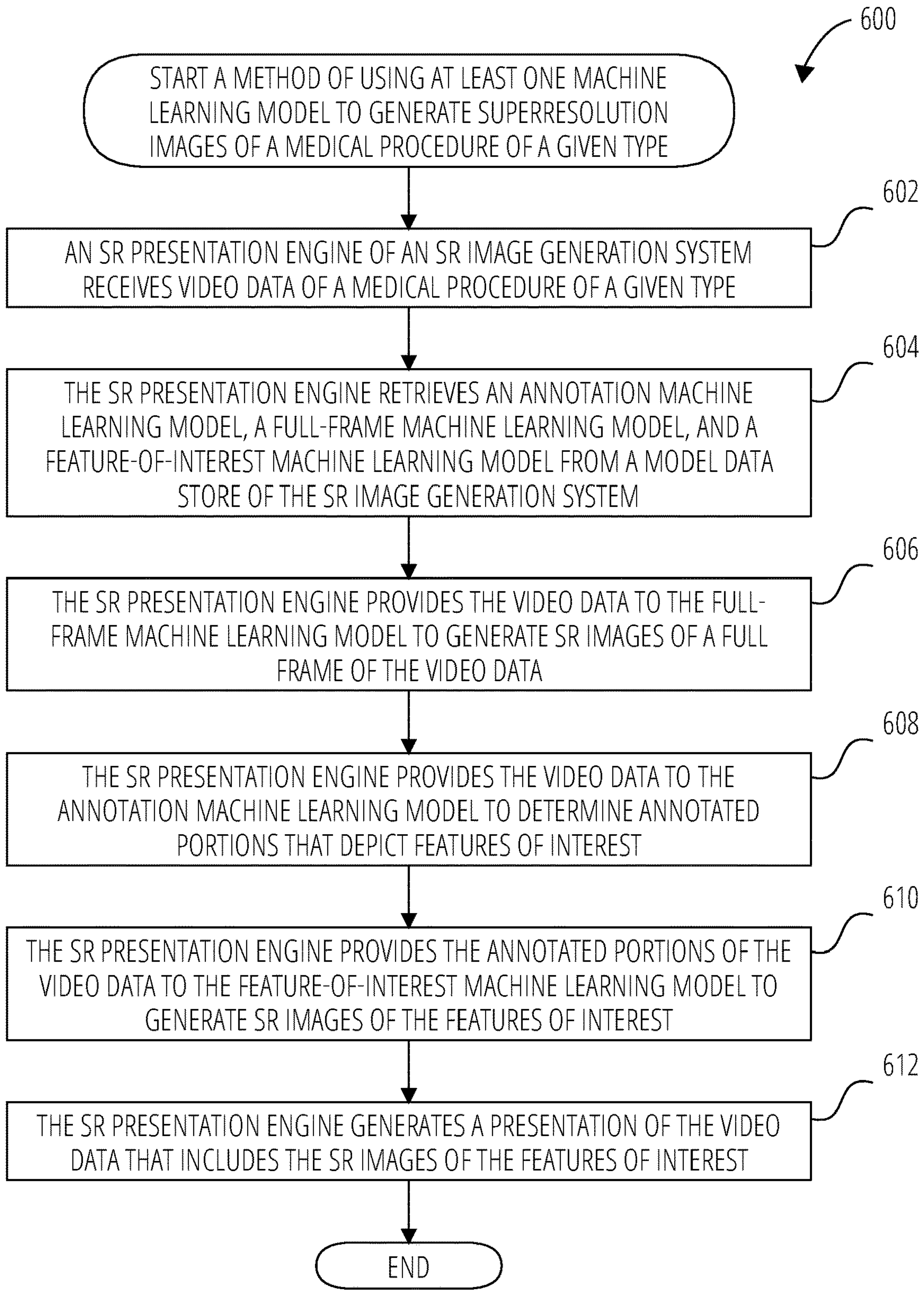
FIG. 6 is a flowchart that illustrates a non-limiting example embodiment of a method of using at least one machine learning model to generate superresolution (SR) images of a medical procedure of a given type according to various aspects of the present disclosure.

FIG. 6 is a flowchart that illustrates a non-limiting example embodiment of a method of using at least one machine learning model to generate superresolution (SR) images of a medical procedure of a given type according to various aspects of the present disclosure. In the method 600, machine learning models trained using video data from medical procedures of the same given type (as discussed above with respect to method 300) are used to generate the SR images.

From a start block, the method 600 proceeds to block 602, where an SR presentation engine 222 of an SR image generation system 202 receives video data of a medical procedure of a given type. In some embodiments, the video data may be received from an endoscope system 100 and the given type of medical procedure may be an endoscopic procedure, including but not limited to a colonoscopy.

At block 604, the SR presentation engine 222 retrieves an annotation machine learning model, a full-frame machine learning model, and a feature-of-interest machine learning model from a model data store 208 of the SR image generation system 202. The full-frame machine learning model and the feature-of-interest machine learning model are machine learning models trained on video data of previous medical procedures of the given type, as discussed above. The annotation machine learning model is any type of machine learning model trained to detect the feature of interest, including but not limited to convolutional neural networks. Since one of ordinary skill in the art is familiar with the training and use of annotation machine learning models, the present discussion does not provide further details on the training and use of such models for the sake of brevity.

The machine learning models may be retrieved based on the given type of medical procedure. For example, the model data store 208 may store machine learning models for multiple different types of procedures, and the SR presentation engine 222 may retrieve appropriate machine learning models for the given type of medical procedure that is taking place. In some embodiments, machine learning models may be trained and stored in the model data store 208 for different types of video data for the given type of medical procedure (for example, for different native resolutions, frame rates, illumination types, or color spaces of video data generated by the endoscope system 100). In such embodiments, the SR presentation engine 222 may retrieve machine learning models that match both the given type of medical procedure and the type of video data being generated by the endoscope system 100. In some embodiments, machine learning models with different levels of performance may be stored in the model data store 208, and the operator may choose between the different levels of performance. For example, a first machine learning model that provides a 2$x$ increase in resolution and a second machine learning model that provides a 4$x$ increase in resolution may both be stored, and the SR presentation engine 222 may choose which one to retrieve based on an operator preference, a system configuration, or using any other suitable technique.

As discussed above, different types of machine learning models may be stored in the model data store 208, and a particular machine learning model may be retrieved by the SR presentation engine 222 depending on a type of presentation to be generated. For example, if a presentation meant to accompany live video during the medical procedure is intended to be generated, then a quick-executing machine learning model, including but not limited to a RAISR model, may be retrieved by the SR presentation engine 222. As another example, if a presentation is intended to be generated offline for review after the medical procedure is completed, then the SR presentation engine 222 may retrieve a machine learning model with a slower execution time but better performance, such as a SABRE model or an ESRGAN model. Further, although both are used for generating SR images, different types of models may be retrieved for the full-frame machine learning model and the feature-of-interest machine learning model.

At block 606, the SR presentation engine 222 provides the video data to the full-frame machine learning model to generate SR images of a full frame of the video data. In some embodiments, the SR presentation engine 222 may generate new full-frame video data based on the output of the full-frame machine learning model. In some embodiments, the SR presentation engine 222 may use the SR images of the full frame as still images.

At block 608, the SR presentation engine 222 provides the video data to the annotation machine learning model to determine annotated portions that depict features of interest. In some embodiments, the SR presentation engine 222 may provide the unprocessed video data received from the endoscope system 100 to the annotation machine learning model. In some embodiments, the SR presentation engine 222 may provide video data based on the SR images output by the full-frame machine learning model at block 606. By providing video data based on the SR images instead of the lower-resolution video data generated by the endoscope system 100, the performance of the annotation machine learning model can be enhanced.

At block 610, the SR presentation engine 222 provides the annotated portions of the video data to the feature-of-interest machine learning model to generate SR images of the features of interest. The SR presentation engine 222 provides the annotated portions of the video data and excludes the remainder of the frame of the video data when providing the annotated portions to the feature-of-interest machine learning model. The intuition here is that the features of interest may have different types of textures to be enhanced when creating SR images than the healthy tissue that makes up the majority of the full frame image, and so providing just the portions of the frame that include the features of interest to the machine learning model trained to enhance those different types of textures will provide a more accurate SR image of the features of interest.

At block 612, the SR presentation engine 222 generates a presentation of the video data that includes the SR images of the features of interest. In some embodiments, the presentation may be provided on the display device 114 of the endoscope system 100 as a live video during the medical procedure. In some embodiments, the presentation may be provided as still images on the display device 114, within a medical record system, on a printout, or via any other suitable technique.

In some embodiments, the presentation may include a live video generated based on the output of the full-frame machine learning model. In some embodiments, the presentation may instead include the original video data from the endoscope system 100. In some embodiments, when the presentation includes a feature of interest, the presentation may include an inset view of a magnified version of the feature of interest. The output of the annotation machine learning model can be used to generate the magnified version of the feature of interest. In some embodiments, the magnified version of the feature of interest may be presented on a separate display device, in a reserved portion of the display device 114, or in a hard copy. In some embodiments, one or more fast machine learning models may be used to generate live video during the procedure, and one or more slower machine learning models may be used to generate offline video or still images after the procedure. In some embodiments, a physician may request that frames or portions of the video data be sent to the slower machine learning models during the procedure, so that results may be obtained and appropriate action can be taken before the procedure has completed.

The method 600 then proceeds to an end block and terminates.

Figure 7A:
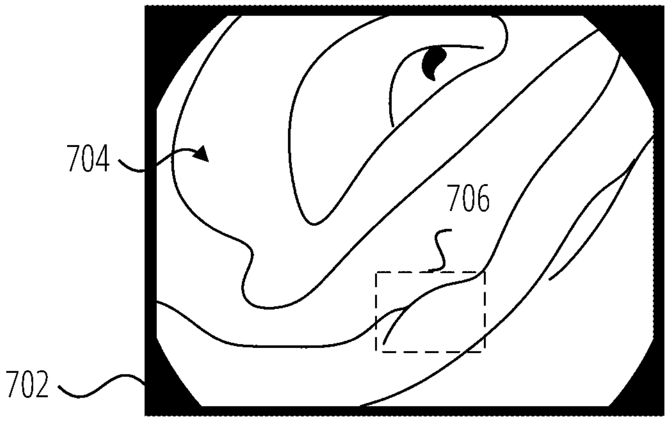
FIG. 7A-FIG. 7C illustrate three different non-limiting example embodiments of presentations according to various aspects of the present disclosure.
Figure 7B:
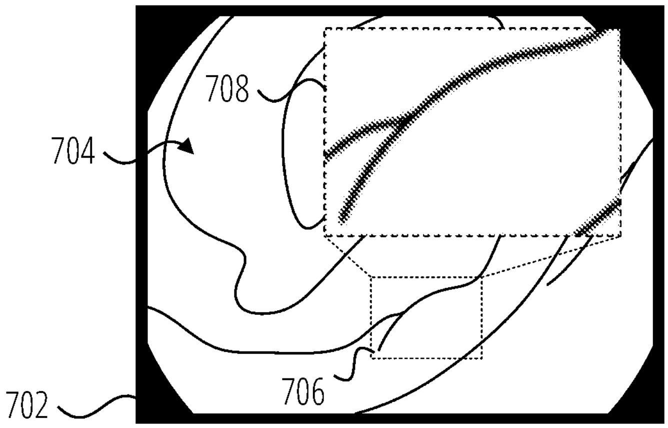
Figure 7C:
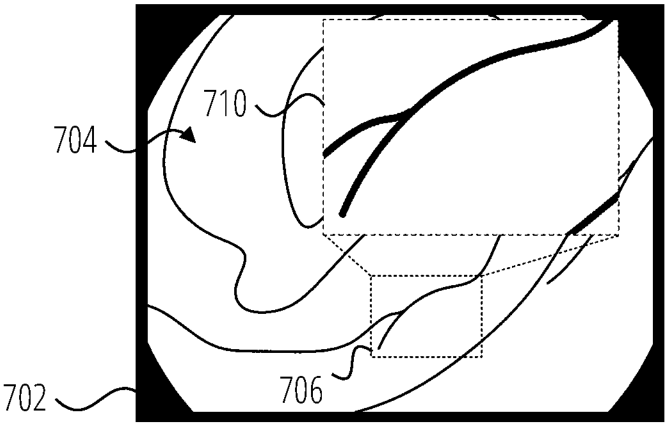

FIG. 7A-FIG. 7C illustrate three different non-limiting example embodiments of presentations according to various aspects of the present disclosure. Each of the presentations shows an example of an image that may be generated during a colonoscopy. In some embodiments, the presentations may be frames of a live video presented during a colonoscopy. In some embodiments, the presentations may be still images included in an after-procedure report, placed within a medical record, or provided in any other suitable format.

In FIG. 7A, a display 702 shows a full frame 704 of an image of a lumen of a colon as viewed from the distal tip 106 of the endoscope 102. In the display 702, an annotated portion 706 is indicated in which a potential polyp has been detected.

FIG. 7B illustrates a presentation that includes a zoomed annotation image 708 without the use of the machine learning models as described above. As shown, the zoomed annotation image 708 is a naively upscaled version of the annotated portion of the full frame 704. As such, though the zoomed annotation image 708 is larger than the annotated portion 706 in the full frame 704, no additional detail is visible. Typically, the zoomed annotation image 708 would appear blurry, smeared, or otherwise not any more helpful in determining a diagnosis than the annotated portion 706 visible without the zoomed annotation image 708.

FIG. 7C illustrates a non-limiting example embodiment of a presentation that includes an SR annotation image 710 generated using the machine learning models as described above. As shown, the SR annotation image 710 is an SR image that includes more textural details than the unzoomed annotated portion 706 in the full frame 704. By providing an SR annotation image 710 instead of merely a naively upscaled image, more details are visible to the physician, and a better diagnosis can be determined.

Though the discussion above primarily discusses the use of visible light information as input to the machine learning models, in some embodiments additional information obtained by the endoscope 102 may also be provided as input to the machine learning models, including but not limited to depth data, position data, orientation data, and polarization data.

Also, although the discussion above primarily relates to endoscopy, one of ordinary skill in the art will recognize that the disclosed techniques could be used on other types of medical imagery, including but not limited to imagery of skin lesions or non-endoscopic imagery of a surgical field.

In the preceding description, numerous specific details are set forth to provide a thorough understanding of various embodiments of the present disclosure. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The order in which some or all of the blocks appear in each method flowchart should not be deemed limiting. Rather, one of ordinary skill in the art having the benefit of the present disclosure will understand that actions associated with some of the blocks may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A non-transitory computer-readable medium having logic stored thereon that, in response to execution by one or more processors of a computing system, cause the computing system to perform actions for automatically generating high-resolution images of features of interest to accompany video data of a medical procedure of a given type, the actions comprising:

providing, by the computing system, the video data of the medical procedure to a first machine learning model trained to annotate features of interest;

providing, by the computing system, annotated portions of the video data to a second machine learning model trained on past images of features of interest to produce superresolution images of features of interest; and generating, by the computing system, a presentation of the video data of the medical procedure that includes the superresolution images of the features of interest produced by the second machine learning model;

wherein the presentation of the video data of the medical procedure that includes the superresolution images of the features of interest includes a zoomed inset version of at least one superresolution image.

2. The computer-readable medium of claim 1, wherein the medical procedure of the given type is a colonoscopy, and the features of interest are polyps.

3. The computer-readable medium of claim 1, wherein generating the presentation of the video data of the medical procedure that includes the superresolution images of the features of interest produced by the second machine learning model includes:

providing the video data of the medical procedure to a third machine learning model trained on video data of past medical procedures of the given type to produce superresolution video data; and generating a presentation that includes the superresolution video data.

4. The computer-readable medium of claim 1, wherein the presentation of the video data is generated during the medical procedure.

5. The computer-readable medium of claim 4, wherein the second machine learning model is a RAISR model.

6. The computer-readable medium of claim 1, wherein the presentation of the video data is generated after completion of the medical procedure.

7. The computer-readable medium of claim 6, wherein the second machine learning model is a SABRE model or an ESRGAN model.

8. A method of automatically generating high-resolution images of features of interest to accompany video data of a medical procedure of a given type, the method comprising:

providing, by a computing system, the video data of the medical procedure to a first machine learning model trained to annotate features of interest;

providing, by the computing system, annotated portions of the video data to a second machine learning model trained on past images of features of interest to produce superresolution images of features of interest; and generating, by the computing system, a presentation of the video data of the medical procedure that includes the superresolution images of the features of interest produced by the second machine learning model;

wherein the presentation of the video data of the medical procedure that includes the superresolution images of the features of interest includes a zoomed inset version of at least one superresolution image.

9. The method of claim 8, wherein the medical procedure of the given type is a colonoscopy, and the features of interest are polyps.

10. The method of claim 8, wherein generating the presentation of the video data of the medical procedure that includes the superresolution images of the features of interest produced by the second machine learning model includes:

providing the video data of the medical procedure to a third machine learning model trained on video data of past medical procedures of the given type to produce superresolution video data; and generating a presentation that includes the superresolution video data.

11. The method of claim 8, wherein the presentation of the video data is generated during the medical procedure.

12. The method of claim 11, wherein the second machine learning model is a RAISR model.

13. The method of claim 8, wherein the presentation of the video data is generated after completion of the medical procedure.

14. The method of claim 13, wherein the second machine learning model is a SABRE model or an ESRGAN model.

15. A computing system, comprising:

at least one processor; and a computer-readable medium having logic stored thereon that, in response to execution by the at least one processor, causes the computing system to perform actions comprising:

receiving video data of a medical procedure;

providing the video data of the medical procedure to a first machine learning model trained to annotate features of interest;

providing annotated portions of the video data to a second machine learning model trained on past images of features of interest to produce superresolution images of features of interest; and generating a presentation of the video data of the medical procedure that includes the superresolution images of the features of interest produced by the second machine learning model;

wherein the presentation of the video data of the medical procedure that includes the superresolution images of the features of interest includes a zoomed inset version of at least one superresolution image.

16. The computing system of claim 15, wherein generating the presentation of the video data of the medical procedure that includes the superresolution images of the features of interest produced by the second machine learning model includes:

providing the video data of the medical procedure to a third machine learning model trained on video data of past medical procedures of the given type to produce superresolution video data; and generating a presentation that includes the superresolution video data.

17. The computing system of claim 15, wherein the presentation of the video data is generated during the medical procedure and the second machine learning model is a RAISR model, or wherein the presentation of the video data is generated after completion of the medical procedure and the second machine learning model is a SABRE model or an ESRGAN model.

* * * * *